United States Patent [19]

Pitt et al.

[11] Patent Number: 5,037,656

[45] Date of Patent: Aug. 6, 1991

[54] POROUS MEMBRANE HAVING HYDROPHILIC AND CELL GROWTH PROMOTIONS SURFACE AND PROCESS

[75] Inventors: Aldo M. Pitt, Sudbury; Michael J. Steuck, North Reading, both of Mass.

[73] Assignee: Millipore Corporation, Bedford, Mass.

[21] Appl. No.: 404,810

[22] Filed: Sep. 8, 1989

Related U.S. Application Data

[60] Continuation-in-part of Ser. No. 286,429, Nov. 19, 1988, Pat. No. 4,908,236, which is a division of Ser. No. 937,755, Dec. 4, 1986, Pat. No. 4,917,793.

[51] Int. Cl.$^5$ .................... A61K 13/00; A61K 31/74; A61K 31/78; C12N 11/00
[52] U.S. Cl. ...................................... 424/443; 424/78; 424/81; 424/484; 424/486; 435/174; 435/180; 435/240.2; 435/240.23; 435/240.241; 435/240.243
[58] Field of Search ................... 424/423, 443, 78, 81, 424/484, 486; 435/240.243, 240.241, 180, 174, 240.2, 240.23; 623/1

[56] References Cited

U.S. PATENT DOCUMENTS

| | | | |
|---|---|---|---|
| 3,276,448 | 10/1966 | Kronenthal | 623/1 |
| 3,910,819 | 10/1975 | Rembaum et al. | 195/1.7 |
| 4,917,793 | 4/1990 | Pitt et al. | 210/94 |

Primary Examiner—Thurman K. Page
Assistant Examiner—G. S. Kishore
Attorney, Agent, or Firm—Andrew T. Karnakis; Paul J. Cook

[57] ABSTRACT

A composite, porous membrane is formed from a porous polymer membrane having desired bulk properties on which is directly coated a cell attachment and/or growth promoting composition and a cross-linked polymer having desired surface properties. The composite membrane retains the porosity of the porous polymeric membrane. In one embodiment, when the substrate is polytetrafluoroethylene the composite is microscopically transparent.

17 Claims, No Drawings

POROUS MEMBRANE HAVING HYDROPHILIC AND CELL GROWTH PROMOTIONS SURFACE AND PROCESS

REFERENCE TO RELATED APPLICATIONS

This application is a continuation-in-part application of Ser. No. 286,429, filed Nov. 19, 1988, now U.S. Pat. No. 4,908,236 which, in turn, is a divisional application of Ser. No. 937,755, filed Dec. 4, 1986, now U.S. Pat. No. 4,917,793.

BACKGROUND OF THE INVENTION

This invention relates to a porous membrane capable of promoting cell attachment and growth and to a process for making the same. More particularly, this invention relates to a microporous or ultrafiltration membrane containing a cell growth promoting substance and is formed from a porous membrane substrate wherein the substrate has its basic properties changed after treatment in accordance with this invention and to a process for forming such a membrane.

As used herein, the term "transparent" means microscopically transparent. That is, the membrane is transparent to the extent that normal sized cells, e.g., 5 to 30 microns, can be viewed through the membrane structure with a microscope such as at 50 times to 600 times magnification. The transparency can be specifically quantified by measuring optical density with visible light such as with a spectrophotometer.

In many applications of membrane technology, it is desirable to utilize a biocompatible membrane filter which is mechanically strong, is thermally stable, is relatively inert chemically and is insoluble in most organic solvents. Often, it is desirable that the membrane have surface properties which are radically different from and sometimes incompatible with the bulk properties set forth above. In some instances it is desired to form a porous membrane which has low non-specific protein binding and which is capable of supporting cell attachment and growth in order that cell morphology can be easily monitored merely by microscopic examination of the live cells on the membrane. For example, in cell growth technology it is desirable to effect cell growth on and within the pores of a membrane rather than on a flat surface so that three dimensional cell growth rather than two dimensional cell growth can be effected. This is particularly true when growing epithelial cells such as those derived from the lungs, kidneys, or intestine which demonstrate a distinct polarity.

In the intact organism, growing cells are surrounded by an extracellular matrix in a porous environment. Cell culture on a microporous membrane substrate allows the cells to achieve both anatomical and functional differentiation. Over the past few decades, the most widely used cell substrate has been impermeable tissue culture plasticware which limits the expression of differentiated properties. The impermeable plastic prevents the diffusion and transport of both nutrients, waste products and hormones from and to the basolateral cell surface. The addition of extracellular matrix (ECM) components to standard plasticware permits cultured cells to assume increased levels of differentiation but the impermeable nature of plastic and the severely restricted access to both cellular domains still limit the types of experimental investigations that can be pursued. The combination of ECM component coating and a microporous membrane substrate, however, provides a powerful new research tool to investigate in vitro cellular structure and function under conditions which closely mimic the in vivo cellular environment.

Prior to the present invention, porous membranes were used for cell growth and the extracellular matrix (ECM) was applied individually to the membrane by the user. In addition, a non-permanent polytetrafluoroethylene membrane coated with noncrosslinked collagen is available from Costar Corporation under the tradename Transwell—COL. Since the collagen is not crosslinked, the collagen coating is not permanent and it gradually leaches from the polymer surface. In addition, this simple coating makes the PTFE membrane transiently hydrophilic and also greatly reduces the porosity and permeability of the membrane. It would be desirable to provide a substrate in the form of a membrane which is ready to use in that it is biologically active, is permanently bound to the membrane, and permanently hydrophilic without the requirement on the individual user to apply an ECM to the membrane.

Accordingly, it would be highly desirable, for example, to provide a composite membrane having both desirable bulk physical strength and chemical resistance while having desired surface properties different from the bulk properties. Furthermore, it would be desirable to provide such a membrane, which exhibits very low non-specific protein adsorption, low or no autofluorescence and which promotes viable attachment and cell growth.

SUMMARY OF THE INVENTION

This invention provides a hydrophilic composite porous membrane comprising a porous substrate having a permanent coating grafted and/or deposited thereon for the entire porous membrane including the inner pore walls which coating has physical and chemical properties different from the bulk properties of the porous membrane and which contains a cell attachment and/or growth promoting composition. The porous substrate can be a hydrophobic or hydrophilic polymeric membrane such as polytetrafluoroethylene, polycarbonate, polyvinylidene fluoride, polypropylene or a polyamide (Nylon). Unlike the composite porous products of the prior art, the coating polymer is directly coated onto the porous substrate without the utilization of an intermediate binding chemical moiety. The surface of the porous composite is hydrophilic and exhibits low or no non-specific protein binding. The composite also has low or no autofluorescence. The cell attachment and growth promoting composition is entrained in the coating and is available to cells which contact the composite. Such a product not only achieves the beneficial properties of a microporous membrane for cell culture, but adds the benefits of having a biological moiety incorporated on the polymer surfaces. The combination of the microporous membrane and the incorporated ECM has a profound effect on observed in vitro cellular differentiation as evidenced by both anatomical and functional markers. It is desirable that such a device is immediately available to the user without further treatment. Surprisingly, the crosslinking process does not inhibit the biological activity of the cell growth or attachment composition. The coating, in fact imobilizes the cell growth or attached composition for use in conjunction with living cells.

DESCRIPTION OF SPECIFIC EMBODIMENTS

In accordance with this invention, a porous membrane such as a polytetrafluoroethylene porous membrane is directly coated throughout its entire surface with a hydrophilic, polymerized, cross-linked monomer having the desired surface properties and having entrained in said coating a cell attachment and growth promoting composition. The monomer is deposited on the surfaces of the porous membrane by graft polymerization and/or by deposition of the cross-linked monomer. Generally, the porous membrane has an average pore size between about 0.001 and 15 microns and more usually between about 0.1 and 5.0 microns. Representative suitable porous membranes include hydrophilic membranes such as polyamides (Nylon) or the like or hydrophobic membranes such as polytetrafluoroethylene, polycarbonate, polyvinylidene fluoride, polysulfones, polyether sulfones or the like. The polytetrafluoroethylene composite membranes have the additional desirable property of being transparent after treatment in accordance with this invention; that is, the optical density on the wet polytetrafluoroethylene has an optical density of between 0 and 0.5, preferably 0 to 0.3 when measured with a spectrophotometer at 410 nanometers visible light. All of the membranes treated in accordance with this invention have the desirable properties of having low or no protein binding, low or no autofluorosence and they promote cell attachment and growth.

The polymerization and cross-linking of the polymerizable monomer to the porous membrane by grafting and/or deposition must be effected so that the entire surface of the porous membrane including the inner surfaces of the pores is coated entirely with a cross-linked/grafted polymer. In one process embodiment, the porous membrane is washed in a first step with a solvent that does not swell or dissolve the porous substrate and which wets the surfaces of the pores. Suitable solvents for this purpose include, for example, methanol, ethanol, 2-propanol, acetone, tetrahydrofuran or the like. The purpose of this wetting step is to assure that the monomer composition subsequently contacted with the porous membrane wets the entire surface of the porous membrane. The membrane then is washed in water. This preliminary wetting step can be eliminated in a second Process embodiment when the solvent composition described below itself functions to wet the entire surface of the membrane. This can be effected when the reagent bath contains a high concentration of organic solvent, generally, between about 80 and 95% by weight. In either the first or second process embodiment all that is required is that the entire porous membrane surface be wet so that a mixture of the cell attachment and growth promoting composition and the polymerizable monomer wets the entire surface of the porous membrane.

Subsequent to wetting the porous membrane, a reagent bath comprising the cell adhesion and growth promoting composition, a free radical polymerizable monomer, a polymerization initiator and cross-linking agent in solvent comprising water or water and a water miscible, polar, organic solvent for these constituents is contacted with the porous membrane under conditions to effect free radical polymerization of the monomer and coating on the porous membrane with a cross-linked polymer. When utilizing a multifunctional cross-linking agent the free radical polymerizable monomer need not be used since the corsslinking agent is capable of being formed into a crosslinked polymer. When the monomer is difunctional or has higher functionality, an additional cross-linking agent need not be utilized. When forming the microscopically transparent polytetrafluoroethylene composite the organic solvent comprises between about 10 and 75 weight, preferably between about 20 and 60 weight percent, based upon the weight of the solution. The microscopic transparency effect is not observed when the solvent is entirely water or entirely organic solvent.

Any monomer for coating the membrane can be utilized herein so long as it is capable of being polymerized by free radical polymerization, can be cross-linked and does not destroy the biological functionality of the cell attachment and/or growth promoting substances utilized. Representative suitable polymerizable monomers include hydroxyalkyl acrylates or methacrylates including 1-hydroxyprop-2-yl acrylate and 2-hydroxyprop-1-yl acrylate, hydroxypropyl methacrylate, 2,3-dihydroxypropyl acrylate, hydroxyethyl acrylate, hydroxyethyl methacrylate or the like or mixtures thereof. Other polymerizable monomers which can be utilized herein include acrylic acid, 2-N,N-dimethylaminoethyl methacrylate, sulfoethyl methacrylate or the like, acrylamides, methacrylamides, ethacrylamides, etc. These monomers are examples of polar-substituted or functionally substituted monomers useful herein.

Suitable initiators and cross-linking agents for the monomers set forth above are well known in the art. For example, when utilizing acrylates as the polymerizable monomer, suitable chemical polymerization initiators include ammonium persulfate, potassium persulfate, 4,4-azobis-(4- cyanovaleric acid), 2,2-azobis (2-amidinopropane) hydrochloride, potassium hydrogen persulfate or the like. In addition to chemical initiation, ultraviolet light, electron beam or cobalt-60 irradiation can be used to initiate polymerization. When utilizing acrylates of methacrylates or methacrylamides as the polymerizable monomer, suitable cross-linking agents include difunctional acrylates, methacrylates or acrylamides such as tetraethylene glycol diacrylate, glycidyl acrylate or methylene bisacrylamide or the like. In one embodiment of this invention , cross- linking agents having difunctionality or higher functionality such as tetraethylene glycol diacrylate can be utilized without an additional monomer in the coating of this invention. The monomer, polymerization initiator and cross-linking agents are contacted with the porous membrane as a mixture in a solvent which is compatible with the three reactants and the porous membrane so that the desired free radical polymerization and cross-linking is achieved without the formation of a significant amount of slowly extractable by-products and without the formation of colored products. If readily extractable by products are formed, these can be removed by conducting a washing step in a suitable solvent subsequent to the coating step.

Suitable cell growth promoting compositions include a collagen, such as Type I rat tail collagen, Type I bovine skin collagen, Type IV collagen, laminin, fibronectin, growth factors such as nerve growth factor, epidermal growth factor, proteoglycans such as glycosaminoglycans, chrondonectin, chondroitin sulfate or mixtures thereof, such as extracts of the EHS (Engelbreth-Holm-Swarm-Tumor) or the like. Lymphokines or immune modulators such as interleukins and interferons also can be utilized. The particular solvent composition employed for the polymerizable monomer, polymerization initiator and cross-linking agent will depend upon the particular reactants employed. All that is necessary is that the reactants are capable of being reacted by free radical initiation in the solvent system and that the solvent does not attack the porous polymer membrane substrate or degrade the cell growth promoting activity. In general, water-miscible, polar, aprotic solvents are most effective in producing transparent, hydrophilic porous substrates. Representative suitable solvent compositions include water or (a) water and (b) a water-miscible organic solvent such as N-methyl-pyrrolidone, dimethyl sulfoxide, 2-propanol, tetrahydrofuran, propylene carbonate, gamma-butyrolactone, tetrahydrothiophene-1,1-dioxide, N-cyclohexyl-2-pyrrolidone, tetramethylurea or the like.

Generally, when used, the polymerizable monomer is present in the reactant solution at a concentration between about 1% and about 20%, preferably between about 3% and about 9% based upon the weight of the reactant solution. The cell growth promoting composition is present in a concentration between about 0.0001%, and 0.3% preferably between about 0.005% and 0.2% based on the weight of the reactant solution. The polymerization initiator is present in an amount of between about 1% and about 35% by weight, based upon the weight of the Polymerizable monomer.

Any conventional energy source for initiating free radical polymerization can be employed such as heating, ultraviolet light, gamma radiation, electron beam radiation or the like. For example, when free radical polymerization is initiated by heating, the reactant solution and the porous membrane are heated to a temperature at least about 60° C. and up to the temperature at which undesirable bulk polymerization occurs in solution or at which the solvent begins to boil. For example, generally suitable temperatures when utilizing an aqueous solvent system are between about 80° C. and about 95° C., preferably between about 88° C. and about 92° C. The polymerization reaction should be effected for a time to assure that the entire exposed surface of the porous membrane is coated without plugging of the pore in the membrane. Generally, suitable reaction times are between about 0.1 and about 30 minutes, preferably between about 1 and about 4 minutes. Reaction can be effected while the porous membrane is immersed in solution. However, this will result in the polymerization of the monomer throughout the solution. It is preferred to saturate the porous membrane with the reactant solution and to effect reaction outside of the solution so that monomer is not wasted. Thus, the reaction can be conducted batchwise or continuously. When operating as a continuous process, a sheet of porous membrane is saturated with the reactant solution and then transferred to a reaction zone where it is exposed to energy to effect the polymerization reaction.

EXAMPLES 1-11

In this example, microporous polytetrafluoroethylene with an average pore diameter of 0.45 micrometer was treated. Eleven aqueous solutions, each containing 25 weight percent N-methylpyrrolidone, were prepared with the compositions listed in Table 1.

Sheets of microporous poly(tetrafluoroethylene), 8"×12", were wet in 2-propanol and exchanged into 25 weight percent aqueous N-methylpyrrolidone. The sheets were then soaked in the treatment solutions described in Table 1. The sheets were then sandwiched between sheets of polyester or polyethylene and exposed to ultraviolet light or heat at 90° C. for two minutes. The sheets were rinsed in water, methanol and then dried.

TABLE 1

| Example No. | % HPA* | % TEGDA* | % AmPS* | Collagen | (Type) | POLYMERIZATION METHOD |
|---|---|---|---|---|---|---|
| 1 | 5 | 1.5 | 1.0 | 0.03 | (RTC) | Heat |
| 2 | 5 | 1.5 | 1.0 | 0.03 | (RTC) | Heat |
| 3 | 5 | 1.5 | 1.0 | 0.03 | (RTC) | UV |
| 4 | 5 | 1.5 | 1.0 | 0.03 | (BSC) | UV |
| 5 | 5 | 1.5 | 1.0 | 0.1 | (RTC) | UV |
| 6 | 5 | 1.5 | 1.0 | 0.2 | (RTC) | UV |
| 7 | 0 | 1.5 | 1.0 | 0.2 | (RTC) | UV |
| 8 | 5 | 1.5 | 1.0 | 0 | | Heat |
| 9 | 5 | 1.5 | 1.0 | 0.1 | (BSC) | Heat |
| 10 | 5 | 1.5 | 1.0 | 0.2 | (BSC) | UV |
| 11 | 5 | 1.5 | 1.0 | 0.2 | (BSC) | UV |

*HPA = mixture of 2-hydroxyprop-1-yl acrylate (75%) and 1-hydroxyprop-2-yl acrylate (25%)
*TEGDA = tetraethylene glycol diacrylate
*AMPS = ammonium persulfate
RTC = Rat Tail Collagen
BSC = Bovine Skin Collagen The sheets were characterized by water rewettability and by light absorbance at 410 nanometers.

The membrane of Examples 1-11 were incorporated by sealing into a hollow tubular cell culture device which then was sterilized by standard 70% ethanol procedures. Madin Darby Canine Kidney (MDCK ATCC NO. 34) cells were cultured in Dulbecco's Modified Eagle's Medium (DMEM) containing 10% fetal bovine serum (FBS), 1% L-glutamine, 1% nonessential amino acids, 100 ug/ml penicillin, 100 ug/ml streptomycin; and 10 uM HEPES. Type I collagen from rat tails (Sigma Chemical Co.) or bovine skin (Vitrogen ® Collagen Corp.) were used as approximately 3 mg/ml solutions in aqueous acid.

Since MDCK cells demonstrate differential adhesion and growth properties depending on the collagen used, the same collagen source on Millicell-CM (Millipore Corporation) was used as the 100% control value. The cells (5.104 cells/cm²) were inoculated into a collagen coated cell culture device comprising a coated Millicell-CM substrate (Millipore Corporation) which is a hydrophilized polytetrafluoroethylene and was used as a control. The seeded devices were incubated at 37° C. in an atmosphere of 7% $CO_2$, 93% air.

The cell growth results were evaluated in comparison with ECM coatings prepared as follows:

A stock solution (3.0 mg/ml) of rat tail collagen (type I) was made in 0.0 N HCl. A stock solution (3.0 mg/ml) of bovine collagen (Type I, Vitrogen Collagen) was obtained from Collagen Corp. (Palo Alto, Calif.). 50 ul of a 1:4 dilution of each 60% ethanol was aseptically applied to the inside of a dry, 12 mm culture plate insert.

The ECM coating was allowed to dry at room temperature in a laminar flow hood before seeding.

The examples in Table 1 were compared to the MDCK cell growth of the appropriate control samples on the days after seeding indicated in Table 2.

TABLE 2

| MDCK CELL GROWTH RESULTS | | | |
|---|---|---|---|
| Example No. | Day 1 | Day 2 | Day 6 |
| 1 | 50 | 50 | 90 |
| 2 | 60 | 75 | 100 |
| 3 | 25 | 75 | 100 |
| 4 | 50 | 90 | 100 |
| 5 | 50 | 60 | 100 |
| 6 | 50 | 50 | 100 |
| 7 | 75 | 100 | 100 |
| 8 | 0 | 0 | 0 |
| 9 | ND* | 50 | 75 |
| 10 | ND* | 50 | 75 |
| 11 | ND* | 100 | 100 |

*Not Determined

MDCK cell growth evaluated with $5 \times 10^4$ cells/cm$^2$ seeded on Day 0 and compared relative to the same collagen source coated on Millicell-CM as ECM coating as the standard method=100%. ND=Not Determined.

We claim:

1. A composite porous thermoplastic membrane which comprises a porous first polymer substrate membrane having an average pore size between about 0.001 and 15 microns, said membrane being directly coated on its entire surface with a collagen and a cross-linked second polymer formed from a monomer polymerized in situ with a free radical initiator and cross linked in situ on said substrate, said composite porous membrane having essentially the same porous configuration as said porous membrane substrate.

2. The composite porous membrane of claims 1 wherein said polymer substrate is polytetrafluoroethylene.

3. The composite porous membrane of claims 1 wherein the polymer substrate is polycarbonate.

4. The composite porous membrane of claim 1 wherein the polymer substrate is a polyamide.

5. The composite porous membrane of claim 1 wherein the polymer substrate is polyvinylidene fluoride.

6. The composite porous membrane of claim 1 wherein the cell growth promoting composition contains Type I rat tail collagen.

7. The composite membrane of claim 1 wherein the cell growth promoting composition contains Type 1 bovine skin collagen.

8. The composite membrane of claim 1 wherein the substrate is polytetrafluoroethylene and the composite is microscopically transparent.

9. The process for forming a composite porous membrane formed from a porous first polymer substrate having an average pore size between about 0.001 and 15 microns, said substrate being directly coated over its entire surface with a collagen and a cross-linked second polymer, said composite porous membrane having essentially the same porous configuration as said porous membrane substrate which comprises:
contacting said porous membrane with a solution of said collagen, a multifunctional monomer of said second polymer, and a free radical polymerization initiator under conditions to polymerize said monomer and to crosslink said second polymer over the entire surface of said porous polymer substrate under conditions to avoid plugging of said pores.

10. The process of claim 9 wherein said polymer substrate is polytetrafluoroethylene.

11. The process of claim 9 wherein said polymer substrate is polycarbonate.

12. The process of claim 9 wherein said polymer substrate is polyamide.

13. The process of claim 9 wherein said polymer substrate is polyvinylidene fluoride.

14. The process of claim 9 wherein said collagen composition contains Type I rat tail collagen.

15. The process of claim 9 wherein said collagen contains Type I bovine skin collagen.

16. The process for forming a composite hydrophilic porous membrane formed from a porous polytetrafluoroethylene substrate having a pore size between about 0.001 and 15 microns, said substrate being directly coated over its entire surface with a collagen and a cross-linked second polymer, said composite porous membrane having essentially the same porous configuration as said porous membrane substrate which comprises:

(a) washing said porous membrane substrate to wet the surfaces of the pores in said porous membrane; and (b) contacting said porous membrane with a solution of a collagen, a monomer of said second polymer, a polymerization initiator and a cross-linking agent for said monomer under conditions to polymerize said monomer and to cross-link said second polymer over the entire surface of said porous polytetrafluoroethylene substrate under conditions to avoid plugging of said pores, said solution comprising between about 10 and 90 weight percent water and between about 80 and 10 weight percent of a water miscible organic solvent.

17. The composite porous product of claim 1 wherein the polymer substrate is polypropylene.

* * * * *